United States Patent
Tysoe et al.

(10) Patent No.: US 7,820,428 B2
(45) Date of Patent: Oct. 26, 2010

(54) PORTABLE LIGHT GENERATION AND DETECTION SYSTEM

(75) Inventors: Steven Tysoe, Ballston Spa, NY (US); Eugene Barash, Niskayuna, NY (US); Thomas Stecher, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 1043 days.

(21) Appl. No.: 11/427,504

(22) Filed: Jun. 29, 2006

(65) Prior Publication Data

US 2008/0003664 A1    Jan. 3, 2008

(51) Int. Cl.
*C12M 1/34* (2006.01)
*C12M 3/00* (2006.01)
*G01J 1/10* (2006.01)

(52) U.S. Cl. .............. 435/287.2; 356/243.1; 356/243.2; 356/243.3; 356/243.4; 356/243.5; 356/243.6; 356/243.7; 356/243.8

(58) Field of Classification Search .............. 435/287.2; 356/243.1–243.8
See application file for complete search history.

(56) References Cited

U.S. PATENT DOCUMENTS

| | | | |
|---|---|---|---|
| 7,172,896 B2 * | 2/2007 | Cheng et al. ............. | 435/287.1 |
| 7,480,042 B1 * | 1/2009 | Phillips et al. ........... | 356/243.1 |
| 2003/0127609 A1 * | 7/2003 | El-Hage et al. ............. | 250/574 |
| 2003/0211479 A1 * | 11/2003 | Howard ........................ | 435/6 |
| 2004/0195598 A1 * | 10/2004 | Tysoe et al. .................. | 257/233 |
| 2005/0064469 A1 * | 3/2005 | Schulz et al. .................. | 435/6 |
| 2005/0170495 A1 * | 8/2005 | Oldham et al. ........... | 435/287.2 |
| 2005/0244932 A1 * | 11/2005 | Harding ..................... | 435/91.1 |
| 2005/0244953 A1 * | 11/2005 | Cohen ..................... | 435/287.2 |

\* cited by examiner

*Primary Examiner*—Walter D Griffin
*Assistant Examiner*—Lydia Edwards
(74) *Attorney, Agent, or Firm*—Mary Louise Gioeni (57) ABSTRACT

A field deployable optical assembly for use in testing a light-responsive sample is disclosed. The assembly includes a microfluidic device, a first optical package, and a second optical package. The first optical package includes a light emitting diode (LED), a first optical device, and a first light-path control, the first optical package configured to guide and focus light from the LED onto the sample. The microfluidic device includes a tethered control substance. In response to a substance within the sample being associated with, and attaching to, the tethered control, the sample emits light. The second optical package includes a photo sensor, a second optical device, and a second light-path control, the second optical package configured to guide and focus the light emitted from the sample onto the photo sensor.

20 Claims, 8 Drawing Sheets

PORTABLE LIGHT GENERATION AND DETECTION SYSTEM

FEDERAL RESEARCH STATEMENT

This invention was made with Government support under contract number W911SR-05-C-0003 by the United States Army RDECOM. The Government has certain rights in this invention.

BACKGROUND OF THE INVENTION

The present disclosure relates generally to a portable light generation and detection system, more particularly to biochemical analysis, and even more particularly to analysis of Nucleic Acid sequences.

There is a need for analyte detection that combines the speed and sensitivity of light-based sensors with the high specificity of bimolecular assays such as nucleic acid hybridization assays. In applications ranging from metabolic diagnostics to detection of pathogenic organisms, biomolecules are typically detected through either nucleic acid amplification or antibody recognition. Signaling is usually accomplished by attaching luminescent labels to probes. These conventional tests are typically difficult to multiplex and require equipment that is bulky, intricate and expensive.

An approach to the detection of pathogens has been to collect a sample of interest and culture the sample on agar plates. This approach, while accurate, is very time consuming and expensive. Additionally, the culture approach requires the samples to be brought back to a laboratory for analysis. Two other common approaches taken by researchers are the use of microarrays and real-time polymerase chain reaction (RT-PCR). While both methods allow for accurate determination of specific nucleic acid sequences, they also lack portability and can be time consuming and expensive to operate.

A number of systems combine the use of light-based sensors with the use of bio-molecular probes. These systems usually involve complex optics to route light to a zone where the probes can interact with the analyte. The cost and complexity renders such systems impractical for routine diagnostics or biohazard monitoring.

Accordingly, there is a need in the art for a nucleic acid analysis arrangement that overcomes these drawbacks.

BRIEF DESCRIPTION OF THE INVENTION

An embodiment of the invention includes a field deployable optical assembly for use in testing a light-responsive sample. The assembly includes a microfluidic device, a first optical package, and a second optical package. The first optical package includes a light emitting diode (LED), a first optical device, and a first light-path control, the first optical package configured to guide and focus light from the LED onto the sample. The microfluidic device includes a tethered control substance. In response to a substance within the sample being associated with, and attaching to, the tethered control, the sample emits light. The second optical package includes a photo sensor, a second optical device, and a second light-path control, the second optical package configured to guide and focus the light emitted from the sample onto the photo sensor.

BRIEF DESCRIPTION OF THE DRAWINGS

Referring to the exemplary drawings wherein like elements are numbered alike in the accompanying Figures.

DETAILED DESCRIPTION OF THE INVENTION

Fluorescence detection methods known in the art are typically carried out on dedicated non-portable (that is, benchtop) equipment. An embodiment of the invention includes a low-cost device for rapid fluorescence analysis performed in the field while maintaining the high performance currently attainable with non-portable equipment.

An embodiment of the invention employs a simple design with a minimum number of parts to minimize costs and weight, thereby providing a portable, compact, point of use optical detector. To optimize light distribution and intensity on a microchannel, an optical package is placed in front of a light source, such as a light-emitting diode (LED) for example. This package may hold a filter designed to optimize the spectral distribution impinging on the microchannel. The package is sized and oriented to match the shape of the microchannel. It is also desirable to collect as much light emanating from the microchannel as possible and to efficiently direct that light to a photo sensor. A second optical package, which has a specific size and shape, is chosen to match the type of photo sensor used.

In an embodiment, the optical packages are configured to hold filters and to collimate and direct light from the source towards the microchannel, and from the microchannel towards the photo sensor. The microchannel holds a sample to be evaluated, which is labeled for example, with a fluorescent dye or a nanoparticle. An excitation light from the light source is turned on and directed towards the microchannel surface by the optical package (such as a light pipe for example). In response to the presence of a nucleic acid of interest being within the sample, the dye will fluoresce, or give off light. Fluorescence from the dye emanates in all directions, and a fraction of this light is collected and guided towards the photo sensor surface via the second optical package. In an embodiment, an optical device is used to help to collect the light and filter out excitation wavelengths, so that they do not contaminate the signal from the dye. All of the abovementioned components are mounted in an optical block, or mount, which determines the optimized optical layout. In one embodiment, the optical packages are oriented at acute angles relative to the microchannel. The angles are determined empirically to optimize the Signal-to-Noise ratio (SNR) for the sample used.

Figure 1:
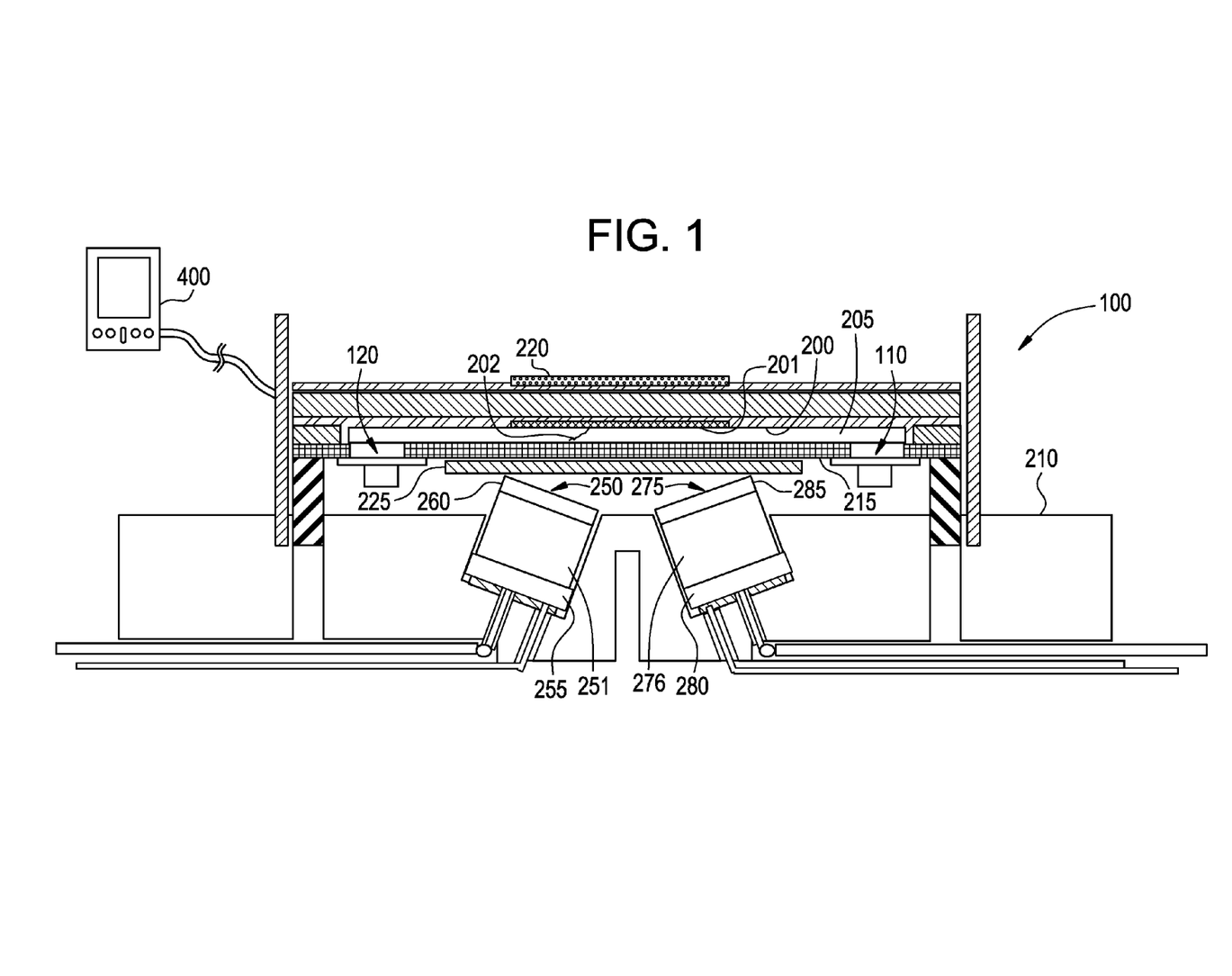
FIG. 1 depicts a schematic of an optical assembly in accordance with an embodiment of the invention.

Referring now to FIG. 1, an exemplary field deployable optical assembly 100 for use in testing a light-responsive sample is depicted. The assembly 100 includes a microfluidic device 200, having a tethered control substance 202, disposed within a sample chamber 205, a clear panel 215, a manual shutter 225, a first optical package 250 having a light emitting diode (LED) 255, a second optical package 275 having a photo sensor 280, a liquid intake 110 and a liquid discharge 120 for providing for injection of the sample to be tested into the sample chamber 205, and an optical mount 210 for mounting of the aforementioned components into the optical assembly 100. The first optical package 250 is disposed and configured to guide and focus light from the LED 255 onto the light-responsive sample within the sample chamber 205, and in response to a substance within the sample being associated with the tethered control 202 and attaching to the tethered control 202, the sample emits light. The second optical package 275 is disposed and configured to guide and focus the light emitted from the sample onto the photo sensor 280.

In an embodiment, a liquid sample including single strands of DNA to be evaluated, along with an indicator dye or nanoparticle is introduced to the sample chamber 205 via the liquid intake 110. The microfluidic device 200 comprises a substrate, such as silicon, upon which a reflective bonding surface 201, such as gold, and the tethered control substance 202 is applied. In an embodiment, the tethered control substance 202 is a synthetic segment of a single strand of DNA with a specific, known sequence of interest attached to the bonding surface 201. It will be appreciated that the single tethered control substance 202 depicted in FIG. 1 is not to scale, and is for illustration purposes only. Furthermore, it will be appreciated that the reflective bonding surface 201 may contain more than the single tethered control substance 202 depicted in FIG. 1. In an embodiment, the microfluidic device 200 comprises a microchannel and a hybridization chamber. In an embodiment, the microchannel is an etched channel within the microfluidic device 200, to provide a flow path for the liquid sample adjacent to the tethered control substance 202. The microchannel has an internal reflectance configured such that light originating from the first optical package 250 is captured within the microchannel. The hybridization chamber is configured such that in response to a substance within the sample being associated with (that is, complementary to) the tethered control 202, the associated substance will attach to the tethered control 202, thereby forming a double strand DNA molecule. The dye is configured to fluoresce (generate light) of a particular wavelength in response to the application of a different wavelength of light in the presence of a double-strand DNA molecule. Therefore, if the sample contains single strand DNA molecules complementary to those tethered to the bonding surface 201, the sample will attach to the tethered control 202, causing the sample and the dye to fluoresce (emit light) in the presence of the appropriate wavelength light. Accordingly, testing for different substances may be accomplished by appropriate selection of the control substances 202 tethered to the bonding surface 201. Additionally, and in an alternative embodiment, in order to test for a plurality of different substances in one sample, the microfluidic device 200 comprises more than one type of tethered control substances 202, which is known as a microarray apparatus. In another embodiment, the microarray apparatus comprises multiple, different, segments of the same tethered control substance 202. In another embodiment, the microfluidic device 200 is separable from the assembly 100 and disposable, allowing the assembly 100 to be easily configured to test for different substances.

While an embodiment of the microfluidic device 200 has been described using a silicon substrate having a gold surface, it will be appreciated that the scope of the invention is not so limited, and that the invention also applies to microfluidic devices having substances and surfaces comprised of other materials that are reflective and suitable to tether the control substance.

In an embodiment, the assembly 100 further comprises a heater 220. The heater 220 is disposed, configured and used in such a manner as to confirm the identity of the sample substance attached to control tether 202. It is understood that a sample that is not a 100% complementary match to the tethered control substance 202 may attach to the control tether 202. In such a case, the assembly 100 would indicate a false positive test result for the presence of the control substance within the sample. It is also understood that the application of heat will cause an attached sample to separate from the control substance 202. The closer a match that the sample substance is to the tethered control substance 202, the greater the temperature required to cause separation. In this way, by measuring the temperature at which the sample separates from the tethered control substance 202, the heater 220 is used to confirm a positive test result.

In an embodiment, the first optical package 250 and the second optical package 275 are mounted within the optical mount 210 on the same side of, and at an angle relative to, the microfluidic device 200. The first optical package 250 includes a light source 255, (also herein referred to as the light emitting diode (LED)), a first optical device 260, and a first light-path control 251. The second optical package 275 includes the photo sensor 280, a second optical device 285, and a second light-path control 276. The first optical package 250 is configured to guide and focus light from the LED 255 onto the sample disposed within the microchannel of the sample chamber 205. The second optical package 275 is configured to guide and focus the light originating, or emitted from the sample disposed within the microchannel onto the photo sensor 280.

In an embodiment, the optical mount 210 comprises one of a metal and a polymer, and the angles of the optical packages 250, 275 are fixed. In an alternate embodiment, the angles of the first and second optical packages 250, 275 relative to the microfluidic device 200 are adjustable in order to allow for fine tuning of the operation of the detector by the user.

In an embodiment, the light source 255 comprises a Group III-V Nitride LED. In an embodiment the photo sensor 280 is one of the following: a Silicon photodiode; a Silicon Carbide photodiode; a positive intrinsic negative photodiode; an avalanche photodiode; a complementary metal-oxide semiconductor device; a charge-coupled device; and a photomultiplier tube. The preceding examples are provided for illustration, not limitation.

Figure 2:
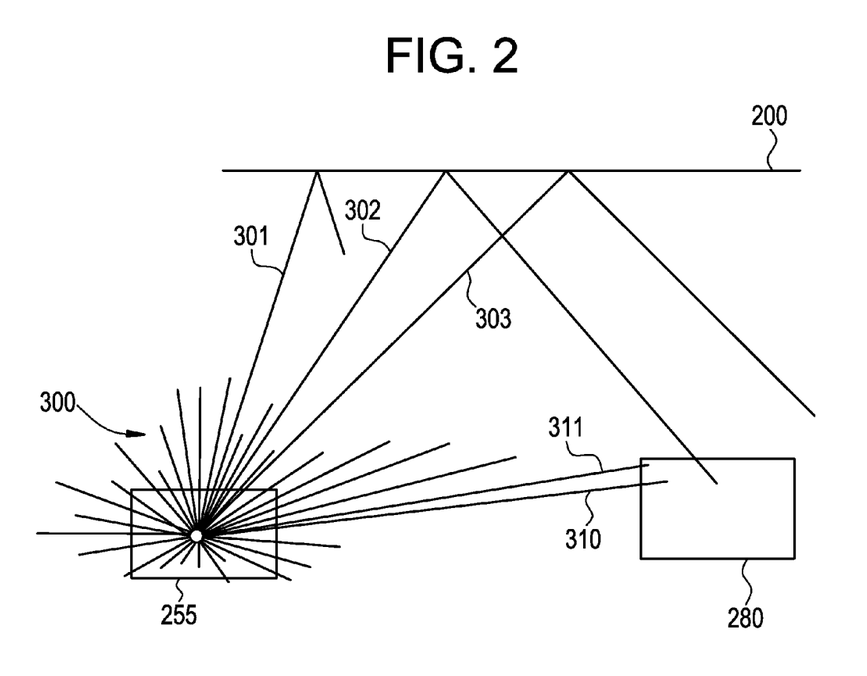
FIG. 2 depicts a schematic of an optical arrangement in accordance with an embodiment of the invention.

Referring now to FIG. 2, a simplified schematic example of the LED 255, photo sensor 280, and microfluidic device 200 is depicted. Light is depicted as emanating out of the LED 255 as a series of lines 300. It will be appreciated that some of the light 301, 302, 303 originating from the LED will strike the microfluidic device 200. Of the light 301, 302, 303 that strikes the microfluidic device 200, only a portion 302 will be reflected such that it strikes the photo sensor 280. Additionally, some of the light 310, 311 originating from the LED 255 will travel directly from the LED 255 to the photo sensor 280. This direct transmission of light is known as cross talk, and is undesirable because it may degrade the sensitivity of the detection and accuracy of the analysis.

Figure 3:
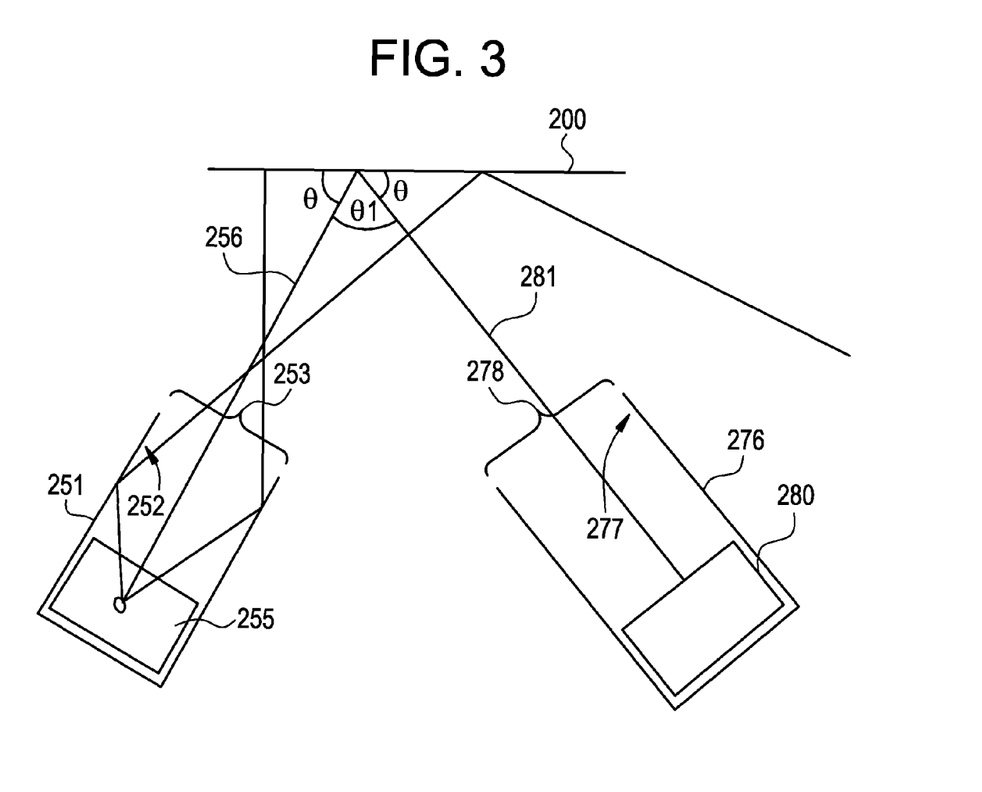
FIG. 3 depicts another schematic of an optical arrangement in accordance with an embodiment of the invention.

Referring now to FIG. 3, a simplified schematic example of the LED 255 and photo sensor 280 employing the first light-path control 251 and the second light-path control 276 is depicted. The first light-path control 251 comprises a first aperture 253 through which the light emitted from the LED 255 is directed. Likewise, the second light-path control 276 comprises a second aperture 278 through which some of the light reflected from the microfluidic device 200 passes as the reflected light is directed to the photo sensor 280. In the art, the light-path controls 251, 276 may be referred to as optical cans. In an embodiment, the first can 251 and the second can 276 are configured and disposed to reduce the direct transmission of light from the LED 255 to the photo sensor 280. The cans 251, 276 are each configured to have an interior surface 252, 277 that is reflective. In an embodiment, the cans 251, 276 comprise one of the following reflective materials: Aluminum; Copper; Silver; Gold; and, Stainless Steel. It will be appreciated from the schematic sketch of FIG. 3 that the first can 251 focuses the light beams from the LED 255 toward the microfluidic device 200. The LED 255, in the absence of the first can 251, provides an unfocused, diverging cone of light distribution. The collimated light beams provided by the first can 251 increases assembly ease and the ability to fine tune the assembly 100. It will be likewise appreciated that the second can 276 is configured to accentuate reception of light that has collided with the microfluidic device 200. In this way, use of the cans 251, 276 will increase the total amount of light arriving at the photo sensor 280 via the microfluidic device 200 while significantly reducing cross talk between the LED 255 and the photo sensor 280.

The increase in total light and elimination of cross talk provided by the configuration of the cans 251, 276 also provides an improvement in the uniformity of the light received at the photo sensor 280. This improved uniformity results in a reduction of the alignment sensitivity of the cans 251, 276.

Referring now back to FIG. 1, in an embodiment, the first optical device 260 and the second optical device 285 are each a lens configured to guide the light waves from the LED 255 and to the photo sensor 280, respectively. In another embodiment, the first optical device 260 is a filter-lens combination configured to collimate the light waves and optimize the spectral distribution of light impinging on the microfluidic device 200, and filter out from the LED 255 the wavelengths of light that will be emitted from the fluorescing attached sample in response to the sample containing the substance complementary to the tethered control 202. In an embodiment, the second optical device 285 is also a filter-lens combination to guide the light waves and filter out excitation wavelengths emitted from the LED 255, so they do not contaminate the wavelength fluorescing from the sample within the microchannel of the microfluidic device 200 in response to the sample containing the substance complementary to the tethered control 202. In an exemplary embodiment, the first and the second optical device 260, 285 comprises only a filter.

Figure 4:
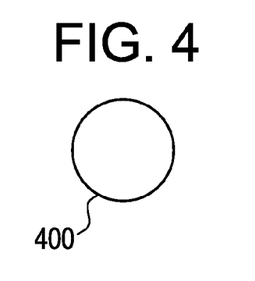
FIGS. 4-7 depict top views of light-path controls in accordance with embodiments of the invention.
Figure 5:
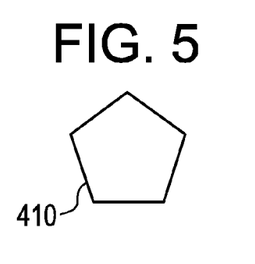
Figure 6:
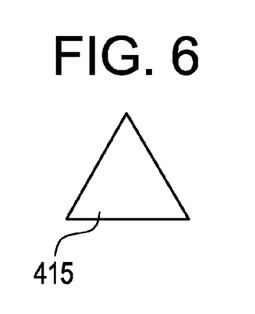
Figure 7:
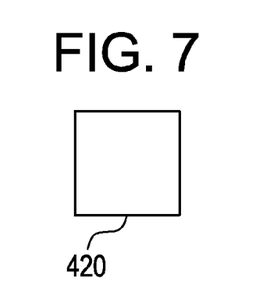

In an embodiment, the first optical device 260 and the second optical device 285 may comprise a variety of components and materials, such as: a spherical lens; a cylindrical lens; a coated Fresnel lens; thin film filter coating; glass; quartz; polycarbonate; and, a polymer material, for example. In an embodiment, the cans 251, 276 may have a variety of shapes, such as: a cylinder 400, a top view of which is depicted in FIG. 4; a pentagonal prism 410, a top view of which is depicted in FIG. 5; a triangular prism 415, a top view of which is depicted in FIG. 6; and, a rectangular prism 420, a top view of which is depicted in FIG. 7, for example. The preceding examples are provided for illustration, not limitation.

In an embodiment, a variety of variables may be adjusted to enhance the performance of the cans 251, 276. One variable that has been determined to increase the beneficial effect of the cans 251, 276 is the angle of orientation of the cans 251, 276 with respect to the microfluidic device 200. This angle is represented by θ in FIG. 3. In an exemplary embodiment, one of the light vectors (represented by the light beams 300 emitted by the LED 255 in FIG. 2) represents a first reference line 256 that is disposed in the center of the first can 251, and defined by the orientation of the first can 251. Similarly, one light vector reflected off of the microfluidic device 200 toward the photo sensor 280 will represent a second reference line 281 disposed in the center of the second can 276, and defined by the orientation of the second can 276. In an embodiment, each reference line 256, 281 is defined by the orientation, or direction, of focused light as it passes through the apertures 253, 278, of the respective first can 251 and second can 276. In an embodiment, each reference line 256, 281 is perpendicular to the plane of the respective aperture 253, 278. In an embodiment, each reference line 256, 281 creates a 30 degree angle, θ relative to the microfluidic device, with a 120 degree included angle, θ1 therebetween. In an embodiment, the reference lines 256, 281 are coplanar.

In an embodiment, another variable affecting the performance of the cans 251, 276 is the distance, or elevation, between the first and second optical packages 250, 275, and the microfluidic device 200. In an embodiment, it is beneficial that the LED 255 illuminate as much of the microchannel disposed within the microfluidic device 200 as possible. In an embodiment, an exemplary microchannel will measure approximately 4 millimeters (mm) by 3 mm. It is likewise beneficial for the photo sensor 280 to be able to collect the fluoresced light from as much of the microchannel as possible. It will be appreciated that selection of any given variable to optimize one result may result in compromise of other results. For example, close disposition of the LED 255 and photo sensor 280 to provide reduced overall assembly 100 size may result in less than optimum illumination of the microfluidic device 200. However, use of the optical packages 250, 275, as described herein, will allow for closer placement of the LED 255 and photo sensor 280 to the microfluidic device 200, (as compared with the absence of the packages 250, 275) thereby reducing the overall dimensions of the assembly 100.

Experimental analysis, summarized in Table 1, has confirmed that the transmission of light, measured as energy in milliwatts (mW), from the LED 255 to the microfluidic device 200, arriving at the photo sensor 280 increases with use of the optical packages 250, 275 including cans 251, 276.

TABLE 1

| Design | (mW) at Photo Sensor |
| --- | --- |
| No Cans | 10 mW |
| Can Design 1 | 16 mW |
| Can Design 2 | 19 mW |

Figure 8:
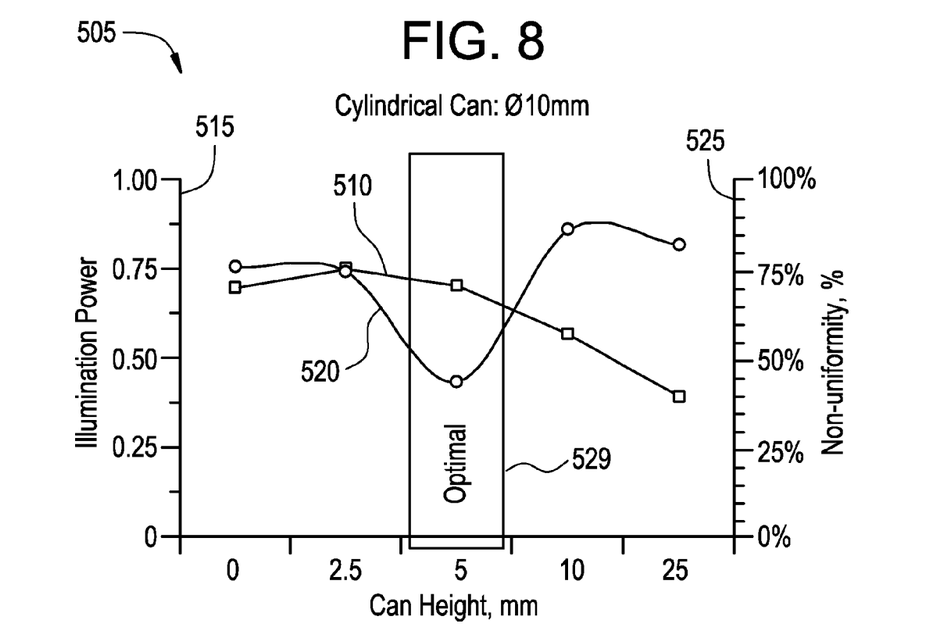
FIG. 8 depicts the effect of light-path control height on operation parameters of the optical assembly in accordance with an embodiment of the invention.
Figure 9:
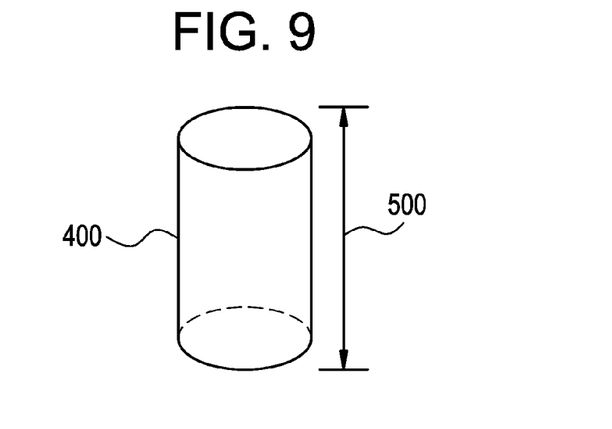
FIG. 9 depicts a front perspective view of a cylindrical light-path control in accordance with an embodiment of the invention.

Referring now to FIGS. 8 and 9, the effects of overall can height 500 of an embodiment of the first can 251 having a cylinder 400 shape and 10 mm diameter, are depicted in graph 505. Line 510 represents the illumination power received at the microfluidic device 200 and relates to the left-side Y-axis 515. Line 520 represents the non-uniformity of light received at the microfluidic device 200, and relates to the right-side Y-axis 525. Can height 500 is represented along the X-axis, with the position "0" representing the performance attained absent use of the can 251. It will be appreciated that it is desired to minimize non-uniformity, and maximize illumination power received at the microfluidic device 200. Accordingly, for the embodiment shown, it will be appreciated that a can height 500 of approximately 5 mm is an optimum 529 height.

Figure 10:
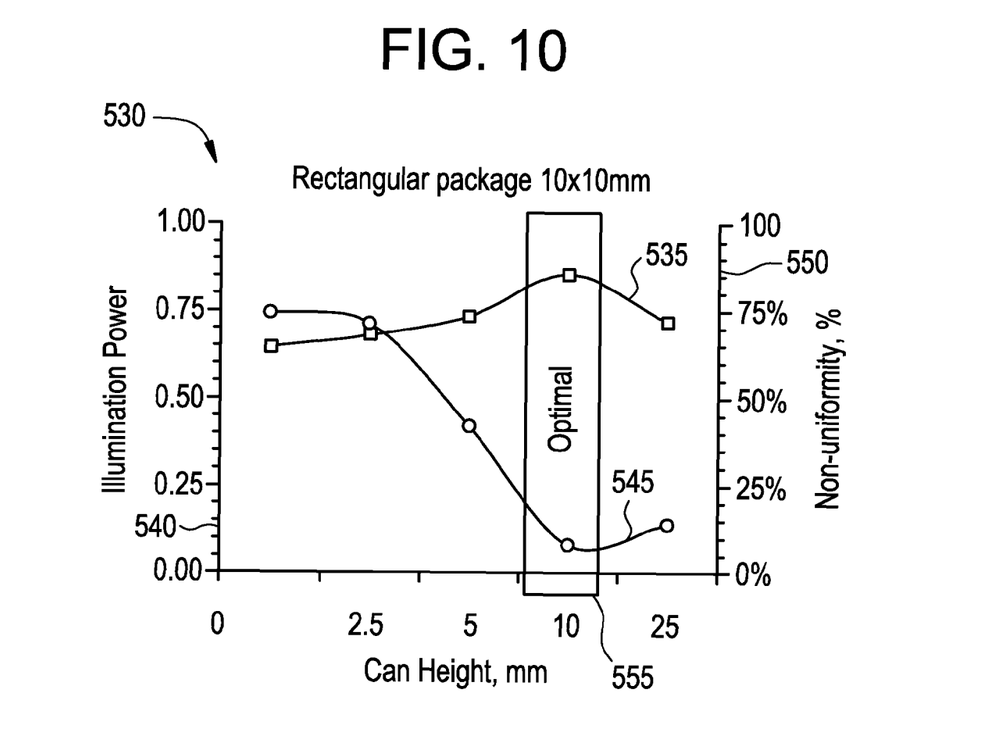
FIG. 10 depicts, in a manner similar to that of FIG. 8, the effect of light-path control height on operation parameters of the optical assembly in accordance with an embodiment of the invention.
Figure 11:
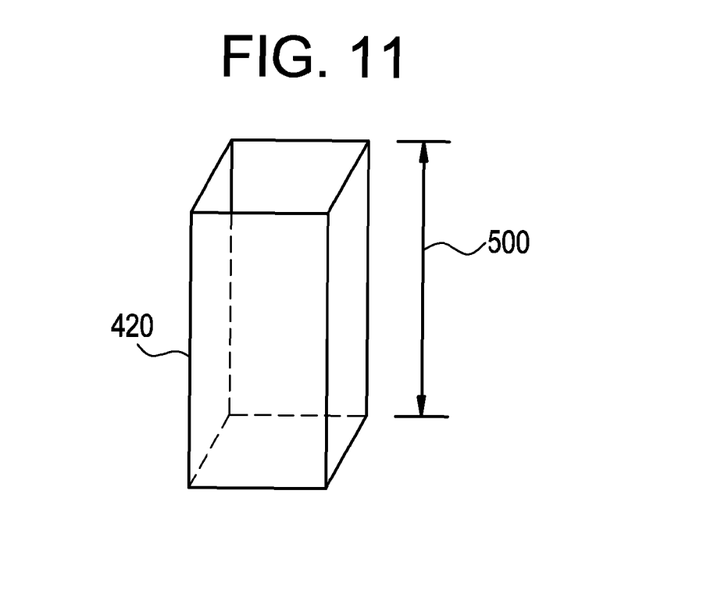
FIG. 11 depicts a front perspective view of a rectangular light-path control in accordance with an embodiment of the invention.

Referring now to FIGS. 10 and 11, the effects of overall can height 500 of an embodiment of the first can 251 having a rectangular 420 10 mm×10 mm shape are depicted in graph 530. Line 535 represents the illumination power received at the microfluidic device 200 and relates to the left-side Y-axis 540. Line 545 represents the non-uniformity of light received at the microfluidic device 200, and relates to the right-side Y-axis 550. Can height 500 is represented along the X-axis, with the position "0" representing the performance attained absent use of the can 251. It will be appreciated that it is desired to minimize non-uniformity, and maximize illumination power received at the microfluidic device 200. Accordingly, for the embodiment shown, it will be appreciated that a can height 500 of approximately 10 mm is an optimum 555 height.

Figure 12:
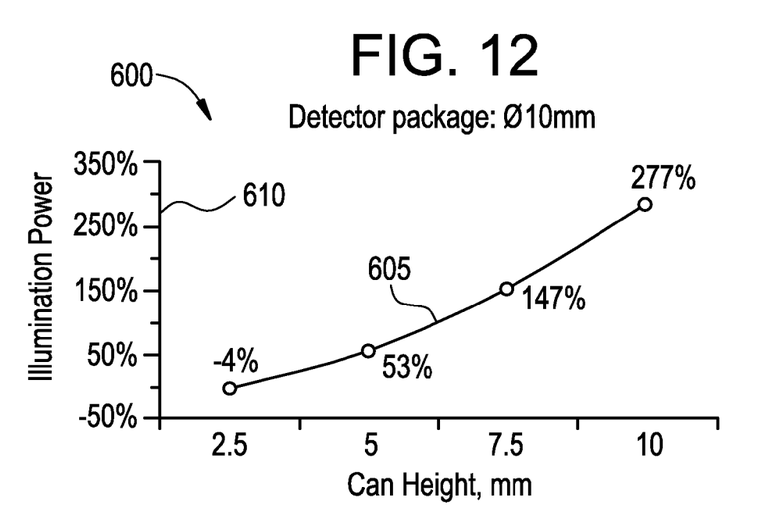
FIGS. 12-14 depict, in a manner similar to that of FIGS. 8 and 10, the effect of light-path control height on operation parameters of the optical assembly in accordance with embodiments of the invention.
Figure 13:
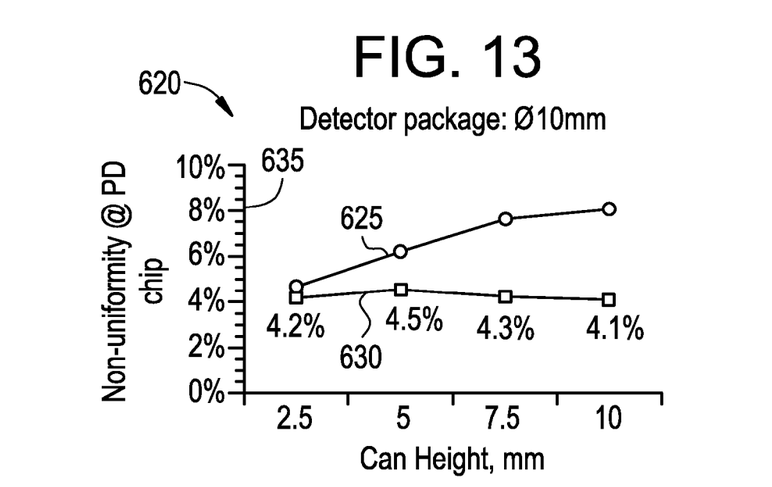

Referring now to FIGS. 12 and 13, with reference to FIG. 9, the effects of overall can height 500 of an embodiment of the second can 276 having cylinder 400 shape and 10 mm diameter are depicted in graph 600 and graph 620. Line 605 of graph 600 represents the illumination power received at the photo sensor 280 and relates to the Y-axis 610. Can height 500 is represented along the X-axis.

Line 625 of graph 620 represents the non-uniformity of light received at the photo sensor 280 in conjunction with a standard photo sensor package absent the features described herein. Line 630 of graph 620 represents the non-uniformity of light received at the photo sensor 280 in conjunction with embodiments of the can 276 as disclosed herein. It will be appreciated that is desired to minimize non-uniformity and maximize illumination power received at the photo sensor 280. Considering the small size of the can 276 desired to minimize the overall size of the optical detector 100, it will be appreciated that the optimum does not exist, as illumination power continues to increase with can height 500.

Figure 14:
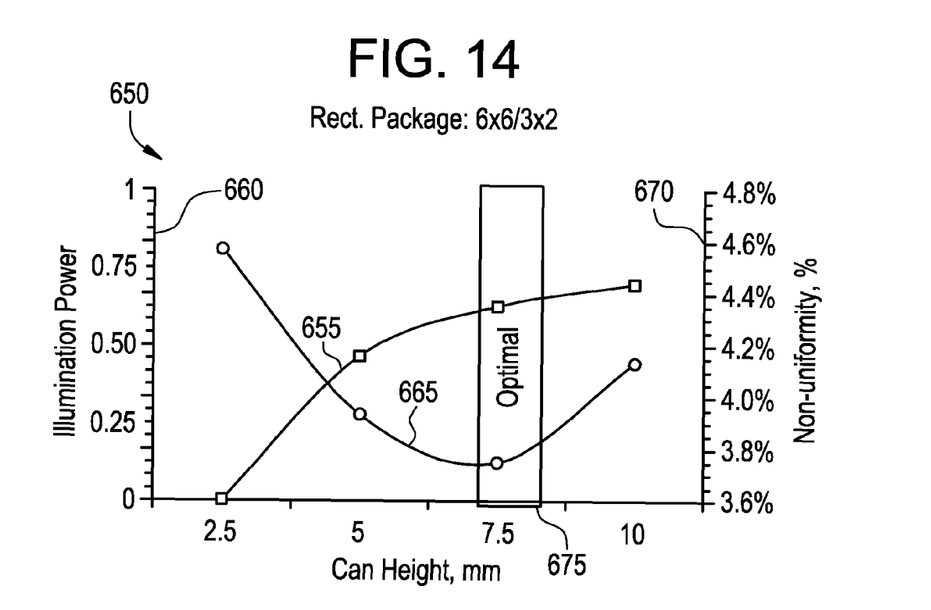
Figure 15:
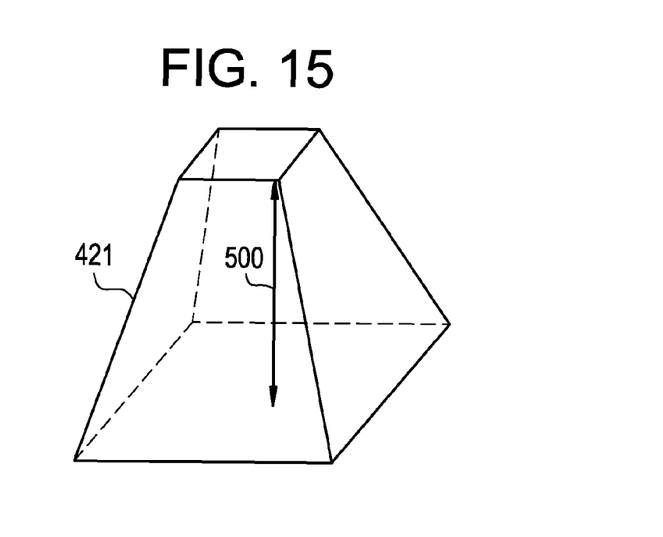
FIG. 15 depicts a front perspective view of a conical rectangular light-path control in accordance with an embodiment of the invention.

Referring now to FIGS. 14 and 15, the effects of overall can height 500 of an embodiment of the second can 276 having a conical rectangular 421 shape are depicted in graph 650. More generally, second can 276 of FIG. 15 may be viewed as having surfaces that taper inward at a distance from the photo sensor 280 disposed proximate the base of the conical shape. Line 655 represents the illumination power received at the photo sensor 280 and relates to the left-side Y-axis 660. Line 665 represents the non-uniformity of light received at the photo sensor 280, and relates to the right-side Y-axis 670. Can height 500 is represented along the X-axis. It will be appreciated that is desired to minimize non-uniformity, and maximize illumination power received at the photo sensor 280. Accordingly, for the embodiment shown, it will be appreciated that a can height 500 of approximately 7.5 mm is an optimum 675 height.

While a variety of can 251, 276 shapes have been considered and discussed, they are intended for illustration only, and not for limitation. It is contemplated that additional can shapes, such as Hexagonal, heptagonal, octagonal, or toroidal, for example, may be beneficial, and are within the scope of the invention. It will be appreciated that the effects of can height 500 have been disclosed for a particular can shape, size, orientation, and disposition. In a similar fashion, the effects of other can 251, 276 variables, such as those listed above, for example may be evaluated to determine their optima.

In an embodiment of a portable, compact, point of use optical detector 100, the total mass of the assembly is less than 7.25 Kilograms (kg), or more specifically, less than 5.5 kg, or even more specifically, less than 3.75 kg. Additionally, in order to provide functionality within the required portable assembly 100, the first can 251 and the second can 276 are each sized to be less than 1 cubic centimeter in volume. This light weight, portable assembly is configured to allow communication, for the storage and display of data, with an external device 400, such as a personal digital assistant (PDA) 400, as depicted in FIG. 1, for example.

While an embodiment of the invention has been described having a metallic can, it will be appreciated that the scope of the invention is not so limited, and that the invention will also apply to cans that may be made of any material that can be made to have a reflective interior, such as metal-plated plastic, for example.

As disclosed, some embodiments of the invention may include some of the following advantages: the ability to use a LED light source and guide the light from LED source to the sample; the ability to provide, collimate and collect light without the need for a lens; and the ability to provide an optical nucleic acid detector suitable for portable use.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A field deployable optical assembly for use in testing a light-responsive sample, the assembly comprising:
   a microfluidic device, the microfluidic device comprising a tethered control substance;
   a first optical package comprising a light emitting diode (LED), a first optical device, a first light-path control, and a first reference line disposed in the center of the first light-path control, defined by the orientation of the first light-path control;
   a second optical package comprising a photo sensor, a second optical device, a second light-path control, and a second reference line disposed in the center of the second light-path control, defined by the orientation of the second light-path control; and
   an optical mount;

wherein the first optical package is configured to guide and focus light from the LED onto the sample;

wherein in response to a substance within the sample being associated with the tethered control and attaching to the tethered control, the sample emits light;

wherein the second optical package is configured to guide and focus the light emitted from the sample onto the photo sensor;

wherein the first optical package and the second optical package are mounted within the optical mount on the same side of, and at an angle relative to, the microfluidic device; and wherein each reference line creating a 30 degree angle relative to the microfluidic device, with a 120 degree included angle therebetween.

2. The assembly of claim 1, wherein:
the first light-path control and the second light-path control are configured and disposed to reduce direct transmission of light from the LED to the photo sensor.

3. The assembly of claim 1, wherein:
the first optical device and the second optical device each comprise one of the following: a filter; a lens; and, a filter-lens combination;
the first optical device and the second optical device each comprise one of the following: glass; quartz; polycarbonate; and, a polymer material;
the first light-path control and the second light-path control each have one of the following shapes: a cylinder; a pentagonal prism; a triangular prism; and, a rectangular prism;
the first light-path control and the second light-path control each comprise one of the following reflective materials: aluminum; copper; silver; gold; and, stainless steel;
the photo sensor comprises one of the following: a Silicon photodiode; a Silicon Carbide photodiode; a positive intrinsic negative photodiode; an avalanche photodiode; a complementary metal-oxide semiconductor device; a charge-coupled device; and a photomultiplier tube;
the lens is one of the following: a spherical lens; a cylindrical lens; and, a coated Fresnel lens; and
the LED comprises a Group III-V Nitride LED.

4. The assembly of claim 1, wherein at least one of the first optical device and the second optical device are coated with a thin film filter.

5. The assembly of claim 1, wherein:
the microfluidic device comprises a microchannel.

6. The assembly of claim 1, wherein:
the microfluidic device comprises a hybridization chamber.

7. The assembly of claim 1, wherein:
the total mass of the assembly is less than 7.25 Kilograms (kg).

8. The assembly of claim 7, wherein:
the total mass of the assembly is less than 5.5 kg.

9. The assembly of claim 8, wherein:
the total mass of the assembly is less than 3.75 kg.

10. The assembly of claim 1, wherein:
the first light-path control and the second light-path control are each less than 1 cubic centimeter in volume.

11. The assembly of claim 1, wherein the angle is a fixed angle.

12. The assembly of claim 1, wherein the angle is an adjustable angle.

13. The assembly of claim 1, wherein:
the microfluidic device is separable from the assembly and disposable.

14. The assembly of claim 1, wherein:
the field deployable assembly is configured to allow data communication with an external device.

15. The assembly of claim 14, wherein:
the field deployable assembly is configured to allow data communication with a personal digital assistant (PDA).

16. The assembly of claim 1, wherein:
the microfluidic device comprises a microarray apparatus.

17. The assembly of claim 1, further comprising:
a heater disposed and configured to confirm the identity of the sample substance attached to the tethered control.

18. The assembly of claim 1, wherein:
the first optical device is configured to filter out wavelengths of light emitted from the sample.

19. The assembly of claim 1, wherein:
the second optical device is configured to filter out wavelengths of light emitted from the LED.

20. The assembly of claim 1, wherein:
the second light-path control comprises surfaces that taper inward at a distance from the photo sensor.

* * * * *